United States Patent [19]

Egen et al.

[11] Patent Number: 5,173,164
[45] Date of Patent: Dec. 22, 1992

[54] MULTI-MODALITY ELECTRICAL SEPARATOR SPPARATUS AND METHOD

[75] Inventors: Ned B. Egen; Garland E. Twitty; David W. Sammons; Rizwan Sharnez, all of Tucson, Ariz.

[73] Assignee: Bioseparations, Inc., Tucson, Ariz.

[21] Appl. No.: 580,959

[22] Filed: Sep. 11, 1990

[51] Int. Cl.$^5$ .................. G01N 27/26; B01D 57/02
[52] U.S. Cl. .................. 204/301; 204/299 R; 204/180.1
[58] Field of Search ............ 204/299 R, 182.3, 183.2, 204/183.3, 301, 180.1

[56] References Cited

U.S. PATENT DOCUMENTS

| | | | |
|---|---|---|---|
| 3,989,613 | 11/1976 | Grizner | 204/182.3 |
| 4,204,929 | 5/1980 | Bier | 204/182.2 |
| 4,673,483 | 6/1987 | Mandle | 204/182.3 |

*Primary Examiner*—John Niebling
*Assistant Examiner*—John S. Starsiak, Jr.
*Attorney, Agent, or Firm*—Rosenbaum & Schwartz

[57] ABSTRACT

A preparative scale multi-mode electrical separator, which is matrix-free and may be operated in both a batch mode and a continuous, flow-through mode is provided. It may be scaled according to the solution quantities which are to be processed. An internal cooling system whereby the process fluid is always in close proximity to a chilled surface assures an efficient heat dissipation during the separation and concentration processes and also allows the use of higher voltage gradients and shorter separation times than prior designs of electrophoretic separators. Electroosmotic mixing is reduced by providing internal, compartmentation of sample fractions, focusing is improved and focusing times are decreased. Different electrophoretic methods, including zone electrophoresis, isoelectric focusing, counterflow gradient focusing or electrodialysis, may be used with the separator. It may be applied to the purification of proteins, ions, and microorganisms, and for water purification.

25 Claims, 3 Drawing Sheets

LEGEND:

▨ BLUE-STAINED HUMAN SERUM ALBUMIN, ABSORBANCE MEASURED AT 602 nm

▨ HUMAN HEMOGLOBIN, ABSORBANCE MEASURED AT 540 nm

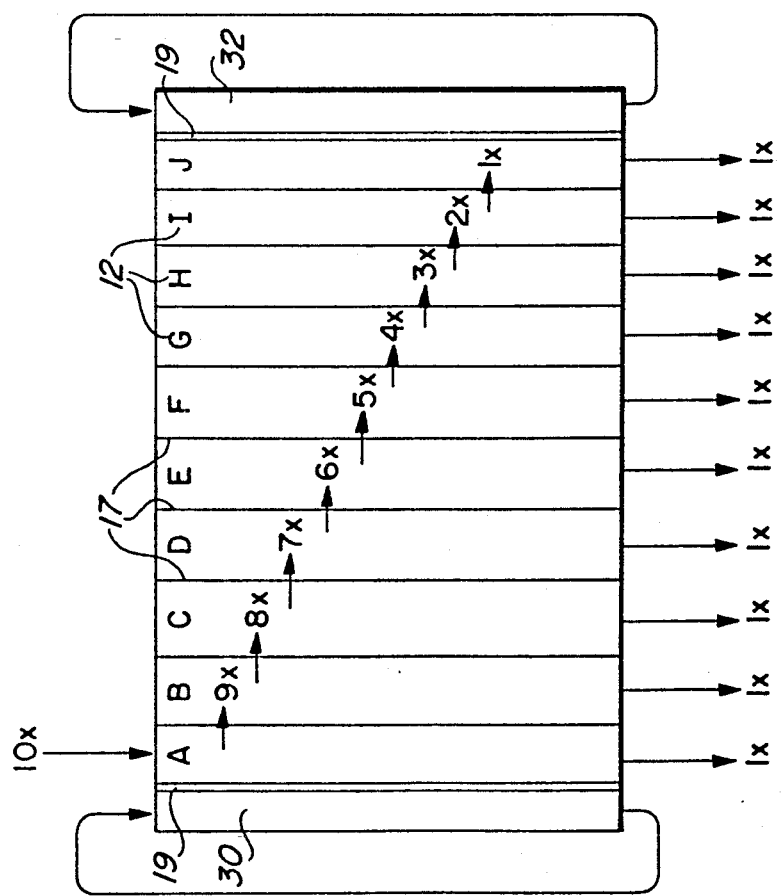
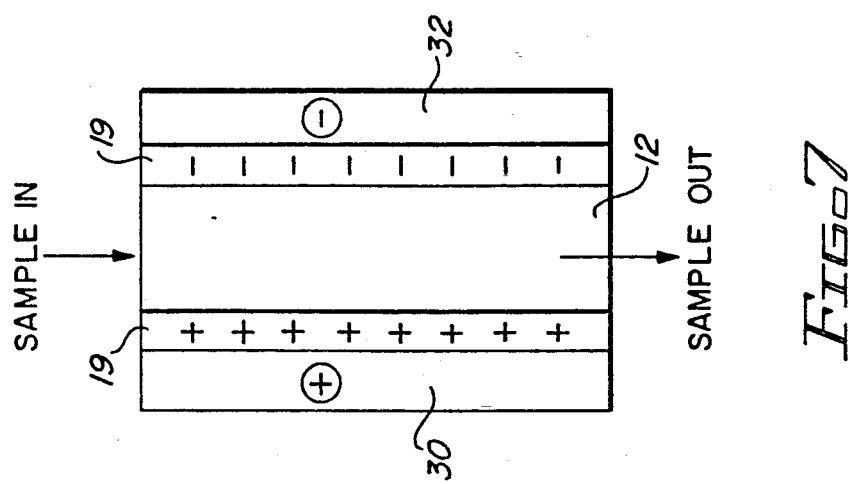

MULTI-MODALITY ELECTRICAL SEPARATOR SPPARATUS AND METHOD

STATEMENT OF GOVERNMENT INTEREST

This invention was made with Government support under Contract NAG8716 awarded by the National Aeronautics and Space Administration. The Government has certain rights in the invention.

BACKGROUND OF THE INVENTION

The present invention relates to an apparatus for conducting separation of biological materials, organic and inorganic compounds or all metal ions from a mixture. More particularly, the present invention relates to an apparatus and method for batch or continuous-flow electrophoretic separation of ionic molecules by zone electrophoresis, isoelectric focusing, counterflow gradient focusing or by electrodialysis.

Electrophoresis is an analytical and preparative tool which can separate components of a mixture on the basis of their ionic charge and mass. A mixture of ionic species is exposed to an applied voltage field, which causes the ions to migrate toward the oppositely charged electrode at a rate which depends on their electrophoretic mobility, which in turn depends on charge, mass and symmetry as well as other parameters. Different modalities of electrophoresis, e.g., zone, isoelectric focusing, isotachophoresis, moving boundary can be utilized in various instruments that are classified by the method selected to minimize convective mixing: 1) free fluid methods which use thin film, shear, capillaries, or compartmentation; or 2) supported fluid methods which use density gradient gels or other matrices. The present method is free fluid compartmentation.

Zone electrophoresis is the separation carried out in the presence of a homogenous buffer, in which sample components separate according to their mobility. No steady state is achieved, and migration continues with gradual broadening of the sample zones due to diffusion and other effects.

Isoelectric focusing (IEF) is a variant based upon the fact that most biomaterials are amphoteric in nature, i.e., are positively charges in an acidic environment and negatively charged in a basic environment. At a particular pH value, called the isoelectric point (pI), the biomaterials acquire a zero net charge due to the balance of positive and negative charges. When such amphoteric materials are exposed to an applied electrical field, in a medium exhibiting a pH gradient, they will migrate toward the pH region of their pI and become immobilized or focused in a steady state at that pH region.

Electrophoretic separation in multi-compartment electrolyzers has been known since 1912, when it was introduced for preparative scale protein fractionation. To the present, the basic apparatus has undergone multiple changes and has been improved in many ways.

Current designs feature membrane-separated, multicompartment electrophoretic cells with cylindrical, annular or rectangular cross-sections, and membrane-separated electrode compartments. The separation process is usually carried out in the free solution under batch process conditions. The entire process volume of the solution may be contained within the electrophoretic cell during the separation process, or the process volume of the solution may be recirculated through the electrophoretic cell until completion of the separation process.

Several electrophoretic devices have been designed by Rilbe, with the latest improved version published in 1980. This latest device consists of a rotating cylinder with 46 subcompartments, each 1.5 cm wide and 12.5 cm in diameter, and has a total volume of 7.6 liters. The subcompartments are separated by polyvinylchloride (PVC) membranes, while, at the ends, one of the electrode compartments is separated by cellophane and the other by PVC. The cooling of the solution is achieved by a combination of inner and outer cooled surfaces. The cylinder is submerged in 360 liters of refrigerated water and rotated about the separation axis, thereby cooling the cylinder walls. Also, four glass cooling tubes pass through each subcompartment and, when the cylinder is rotated about its longitudinal axis, water is scooped into one side of the cooling tube and forced out the other.

While the internal cooling system is a beneficial feature of the apparatus, the choice of materials for the membranes and the excessive width of the subcompartments are disadvantageous. PVC exhibits a 5-10 fold greater electroosmotic effect than a woven monofilament nylon screen. Electroosmotic mixing is also increased by the small porosity of the PVC membranes, which trap colloidal and larger protein particles. PVC also binds proteins with considerable affinity. Protein precipitations at a position in the pH gradient, deviating from the respective pI, produce a net charge on the immobilized protein resulting in electroosmotic mixing. By using the chosen membrane materials, i.e., cellophane and PVC, electroosmotic transport occurs across the electrode membrane, which induces mixing. Electroosmotic transport counteracts and degrades the separation process. The large width of each subcompartment also retards the separation process. Also, the low ionic strength electrolytes, which are employed in Rilbe's apparatus, cause a voltage drop in the electrode chambers, which decreases the effective field strength in the separation compartments.

Another typical device for electrophoretic separation processes is disclosed in U.S. Pat. No. 4,588,492 issued May 13, 1986 to Bier. This apparatus, known by the trademark ROTOFOR, is essentially a smaller version of the apparatus by Rilbe. It consists of twenty annular-shaped compartments, which are arranged into a cylindrical electrophoretic cell. The individual compartments are separated by membranes, and an internal cooling tube is arranged along the longitudinal axis of the cell. The cell is usually operated in a horizontal position while rotated along its longitudinal axis. It has recently been demonstrated by Egen, N. B., et al., "Fluid Stabilization Studies of Free IEF in Cylindrical and Annular Columns", *Separation Science & Technology*, Vol. 22, p. 1383 (1987), however, that equal separation results could be achieved in a vertical stationary mode while minimal separation was observed in a horizontal stationary operation mode. The ROTOFOR eliminates some of the drawbacks of Rilbe's device by using woven nylon screen, small width subcompartments and ion exchange membranes to separate the electrode compartments. The disadvantage of the ROTOFOR is that, due to the annular cross section and the central inner cooling tube, scale-up to significantly larger capacities is impossible, since an increase of the cylinder diameter would result in an insufficient cooling of the solution close to the outer walls of the cylinder.

The ROTOFOR is strictly a batch mode processor and cannot be operated in a continuous flow mode.

Multi-compartment electrolyzers which separate proteins by the principles of IEF are also known. For example, U.S. Pat. Nos. 4,362,613 and 4,204,929, both issued to M. Bier on Dec. 7, 1982 and May 27, 1980, respectively, disclose such apparatus. However, this is designed to operate exclusively by IEF and in the batch mode, whereby the solution is recycled between the electrolytic cell and an external heat exchanger to provide external cooling of the sample solution.

A method for the continuous-flow electrophoretic separation of proteins, antibodies, nucleic acids etc. in a matrix system is known and is shown in U.S. Pat. No. 4,323,439 issued to P. O'Farrell on Apr. 6, 1982. Matrices of the size-exclusion type, of the ionic type, of the adsorption-type or of a special affinity to the particles to be separated are used. The separation chamber comprises at least one matrix of continuously varying properties or two and more matrices of continuously or intermittently varying properties in the longitudinal direction. The mixture to be separated is introduced into the separation chamber in a carrier liquid which flows through the length of the chamber. An electric field is applied such that the electrophoretic movement occurs in a direction opposite to the carrier liquid flow. By countering the electrophoretic movement with counter-current flow, an equilibrium zone within the chamber is created, where the separated and concentrated ions may be withdrawn. However, matrices are expensive and the random withdrawal of the separated and concentrated ionic species will cause flow discontinuities. An electrophoretic separator in a continuous flow, free solution mode is highly desirable.

SUMMARY OF THE INVENTION

It is, therefore, an object of the present invention to provide a preparative scale, free-fluid electrical separator, which is matrix-free, which may be operated in both a batch mode and a continuous, flow-through mode and which may be scaled according to the solution quantities which are to be processed. It is another object of the present invention to provide the electrical separator with an internal cooling system to efficiently dissipate Joule heat during the separation processes, which eliminates the need for horizontal rotation or recirculation to an external cooler, and permits application of higher voltage gradients and yields shorter separation times. Another broad aspect of the invention is to provide an apparatus for electrical separation of biological materials, organic and inorganic compounds, and metal ions, by a single apparatus adaptable for use in zone electrophoresis, isoelectric focusing, counter-flow gradient electrophoresis and electrodialysis.

The continuous flow electrical separator of the present invention is primarily characterized by narrow and long separation chambers defined within planar spacers having internal heat exchange means, which form two parallel side walls of each separation chamber. A plurality of spacers may be arranged next to each other to form an array of parallel spacers having horizontally aligned separation chambers. Membranes, selected according to desired separation process, are provided between the planar spacers to separate the separation chambers, act as containing walls for fluid within the separation chambers and minimize convective mixing of the separated sample zones defined within each separation chamber. An electrode compartment is provided at each end of the spacer array, containing an anode and a cathode and appropriate anolyte and catholyte, respectively. A multichannel pump introduces the unprocessed sample into the individual separation chambers and pumps processed fluid from each separation chamber to a collection chamber.

The electrical separator of the present invention allows for a modular design which may be adjusted to the respective needs of various applications. It may be used for separations based on electrophoretic methods such as, without limitation, zone, counter-flow gradient, IEF, continuous flow electrodialysis, electrodecantation and for water purification based upon any of these methods.

These objects and other features and advantages of the present invention, will appear more clearly from the following more detailed description of the preferred embodiments thereof taken with reference to the accompanying figures.

BRIEF DESCRIPTION OF THE DRAWINGS

FIG. 6 diagrammatically illustrates the process of counter-flow gradient focusing according to the present invention.

FIG. 7 diagrammatically illustrates the process of electrodialysis according to present invention.

DESCRIPTION OF PREFERRED EMBODIMENTS

Figure 3:
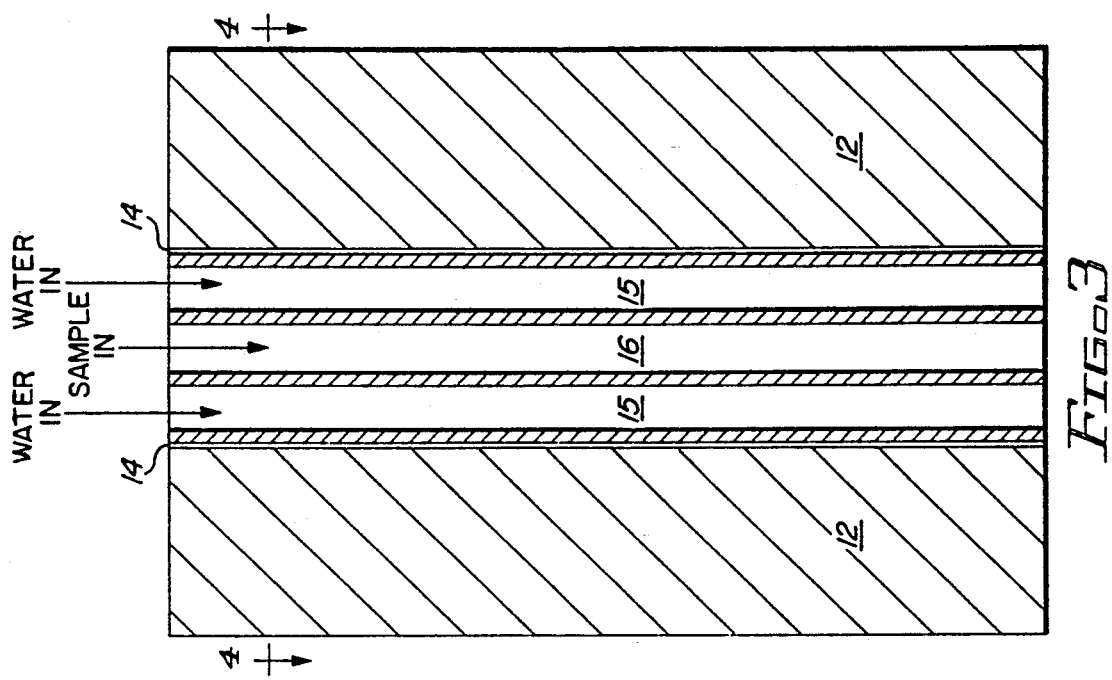
FIG. 3 is a cross-sectional view taken along line 3—3 of FIG. 1.
Figure 2:
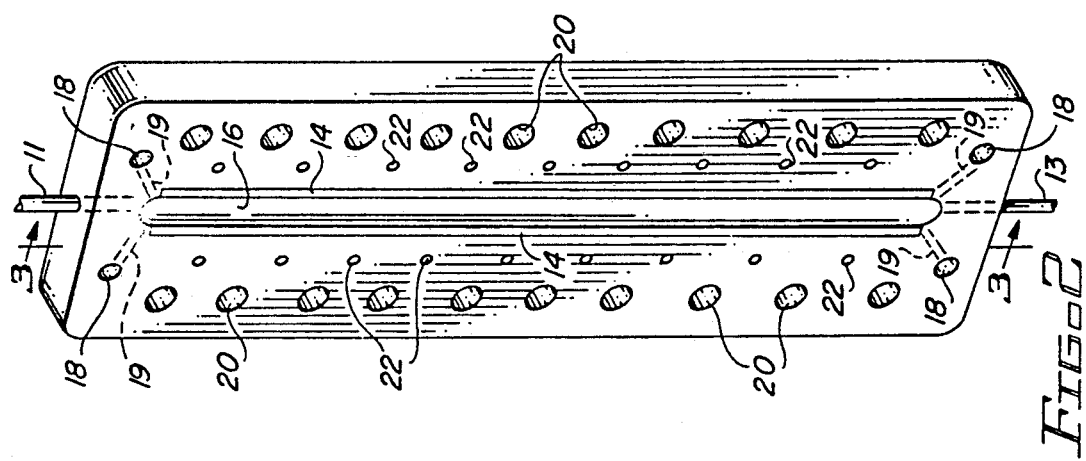
FIG. 2 is a perspective view of a separation cell according to the present invention.
Figure 1:
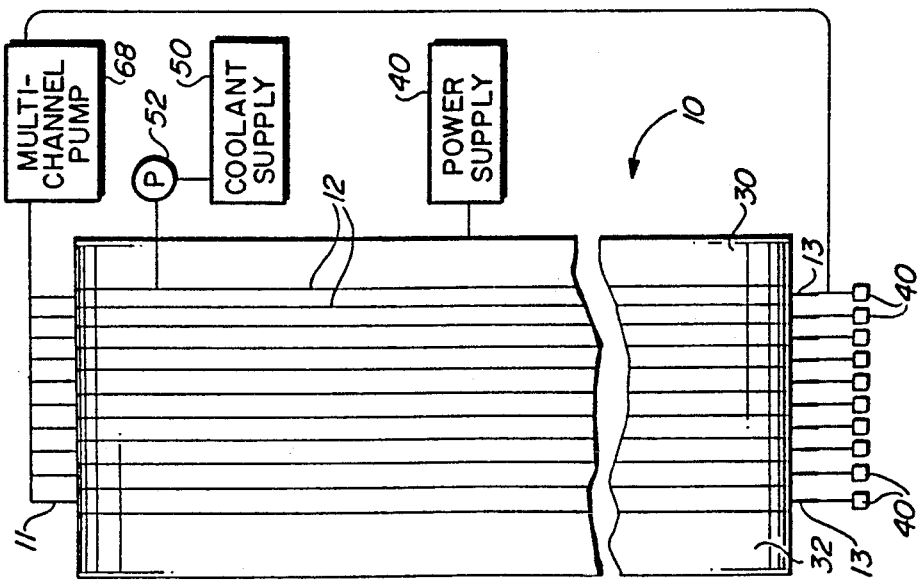
FIG. 1 is a diagrammatic view of the separation apparatus according to the present invention.
Figure 4:
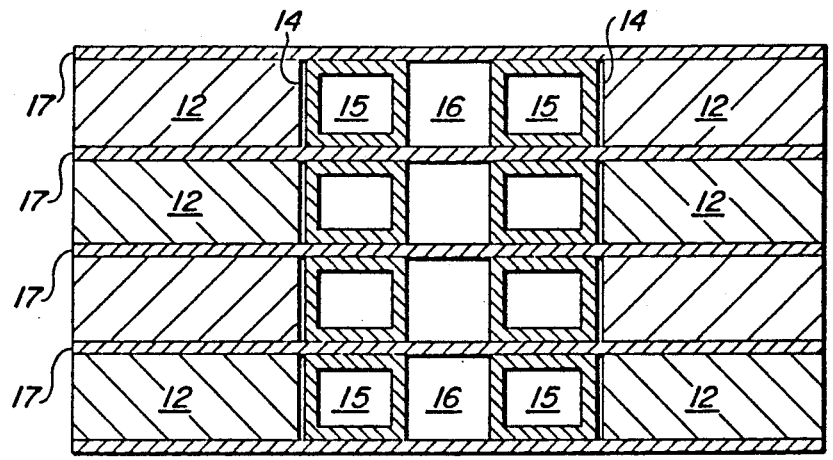
FIG. 4 is a cross-sectional view illustrating multiple adjacent separation cells according to the present invention.

Turning to the accompanying Figures, and with particular reference to FIGS. 1-4, there is shown a multicompartment electrophoretic separator 10 according to a preferred embodiment of the present invention. The electrophoretic separator is comprised of an array of subcompartments 12 with two electrode compartments 30, 32 on either end of the array. All subcompartments 12 for this electrophoretic separation cell are identical. Each subcompartment 12 consists generally of a planar body which has a narrow channel 16 formed within the planar body. Channel 16 acts as the separation chamber for processing the sample. The subcompartments 12 are adjacently arrayed in a co-planar fashion. Membranes 17 are interdisposed between the individual subcompartments 12. Membranes 17 which serve as delimiting inter-subcompartmental boundaries for the narrow channel 16 and effectively separate each adjacent channel 16 into discrete separation chambers.

Each subcompartment 12 is provided with a linear array of openings 20 which receive a bolt or other fastening means to clamp together the array of aligned subcompartments 12. Each subcompartment also is provided with a linear array of alignment openings 22, which receive alignment pins to maintain a uniform width of the channel 16 along its longitudinal aspect. The array is bolted or clamped together, whereby the electrode compartments function as end-plates which provide a rigid structural support. With the electrode compartments 30, 32 provided on either end of the array, an electrical field applied to the electrophoretic separator runs perpendicular to the planar aspect of subcompartments 23 and the membranes 17. Appropriate electrolytes are pumped into their respective electrode compartments. Continuous recycling of the electrolytes removes electrolytic gases.

The membranes 17 reduce inter-subcompartmental fluid convection and mixing of the separated sample zones. By providing a parallel array of membranes 17 perpendicular to the separation axis confines fluid convection to the individual subcompartments 12, which is beneficial to the separation process while preventing detrimental fluid convection between subcompartments 12.

Each subcompartment 12 is provided with a heat exchanger 14 to dissipate Joule heat generated during the electrophoretic separation. The heat exchanger 14 is disposed in the channel 16 of each subcompartment 12 such that at least a substantial portion of the longitudinal inner walls of channel 16 formed by the planar body 12, are associated with heat exchanger 14. According to the preferred embodiment of the invention, heat exchanger 14 comprises either a quadrilateral or circular cross-sectional tubing having a depth or diameter corresponding to the thickness of the planar body 12 and a lumen 15. The heat exchanger 14 connects to inlet and outlet ports 18 at the ends of the length of the cavity. Inlet and outlet ports 18 are preferably formed by providing co-axially aligned inlet and outlet ports 18 in adjacent arrayed subcompartments 12, each port 18 having fluid conduit 19 between the port 18 and the heat exchanger 14. Fluid conduit 19 may be an integral with heat exchanger 14 or a discrete component.

Sample inlet 11 and collection 13 ports are also provided at each end of channel 16 and are in fluid flow communication therewith. Both inlet port 11 and collection port 13 are connected to a multichannel pump 60 which pumps the sample solution into channels 16 of individual subcompartments 12 and concurrently removes separated solution from the collection ports 13.

The volume of the electrophoretic separator according to the present invention is determined by the number of subcompartments 12 and the length of channel 16 in each subcompartment 12.

According to the best mode contemplated for the invention, each subcompartment 12 is preferably 0.1 to 0.4 cm in thickness, and may be die cut, extruded, molded or otherwise formed as may be known in the art. Regardless of the length of channel 16 or number of subcompartments 12, the thickness of the each subcompartment 12, and, hence, channel 16, i.e., the distance between two membranes 17, should be about 0.1 to about 0.4 cm. A thickness of excessive width is detrimental to the electrophoretic separation process due to the greater time required for a particle to cross each subcompartment. A thickness which is too small makes sample input and output difficult and may allow adjacent membranes to touch, thereby occluding flow through the channel 16. The length of the planar body 12 and cavity 16 may vary to accommodate different volumes. A greater distance between the sample inlet and exit ports requires unnecessary fabrication costs. A much shorter path between the sample inlet and exit ports, on the other hand, does not provide enough travel distance for an effective separation. Further, an effective dimension of the channel 16 which forms the separation chamber, should be about 50 cm in length, 0.2 cm in width and 0.3 cm in thickness, which yields an effective total volume of 3 ml within channel 16.

Because of its dielectric properties, a silicone rubber material is well suited for sample containment in an electrophoretic separator, however, other electrically insulating materials are also effective. Because of its elastic properties, silicone rubber, together with the membranes 17, acts as a gasket between adjacent subcompartments 12 when the subcompartment array (FIG. 1) is bolted or clamped together.

The membranes used in the embodiment of the present invention are preferably woven monofilament nylon screens. Compared to PVC screens, frequently employed in electrophoretic separators of the prior art such as the Rilbe machine, nylon screens lower intercompartmental electroosmosis by a factor of 5 to 10.

The electrode compartments 30, 32, provided at each end of the subcompartment array, provide a cavity for a platinum electrode. The electrode compartments 30, 32 are constructed from a suitable plastic material, preferably acrylic, and serve as a rigid end plate allowing the subcompartment array to be bolted together. In order to remove electrolytic gases from the electrolytic cavity, they are equipped with inlet and exit ports for the flow-through operation of the electrolytes. The electrolytes may be recirculated within each compartment 30 or 32, may be flowed through each compartment 30, 32 in a single pass or the anolyte may be mixed with the catholyte.

To facilitate assembly of the apparatus 10, the subcompartments 12, and the electrode compartments 30, 32, have a plurality of openings perpendicular to their flat faces. Bolts are inserted into the openings, which form one long bore hole upon the co-axial alignment of the components, which tightened to seal the subcompartments and electrode compartments against leakage. Additionally, a plurality of alignment openings 22 are provided in the planar bodies 12 and adjacent to or in close proximity to the channel 16. The alignment openings 22 serve to maintain uniform longitudinal alignment of channel 16, by engagement upon alignment pins (not shown).

Sample inlet 11 and collection 13 ports may be disposed within the silicone rubber material and pass from each end of the channel 16 and extend external to the planar body of the subcompartment 12. Each of the sample inlet 11 and collection 13 ports are connected to the multichannel pump 60.

Continuous-flow processing requires the provision of means for dissipating the Joule heat generated by the applied electric field. The apparatus of the present invention has the heat exchange means 14 for the recirculation of a coolant either attached to, or made a part of the planar body of each subcompartment 12 such that the heat exchange means 14 forms side walls of channel 16. The heat exchange means 14 according to the preferred embodiment of the invention, consists of cooling tubes having the same cross-sectional diameter or depth as that of the channel 16. Each subcompartment 12 is equipped with a parallel pair of cooling tubes 14, each of which has inlet and exit ports 18 provided at the ends of the longitudinal axis of the subcompartment 12. The inlet and outlet ports 18 of all subcompartments 12 open into the same feed lines running perpendicular to the planar aspect of each subcompartment 12 through the array. The feed lines on either end of the silicone rubber spacer are formed by openings perpendicular to the planar aspect of the planar body of each subcompartment 12 and are in fluid flow communication upon bolting or clamping of the subcompartment array. The coolant is supplied from a coolant supply 50 and is continuously recirculated by a pump 52.

To achieve an optimized cooling effect, the cooling tubes 14 are thin walled, achieving high thermal transfer rates, and have high dielectric strength to avoid electrical conduction to the coolant. Suitable materials are thin plastic materials, such as tetrafluoroethylene or fluorinated ethylpropylene resins marketed under the trademark TEFLON or polypropylene co-polymers, polyethelyene or silicone. The cooling tubes 14 may have any suitable cross-sectional shape, but are preferably circular or quadrilateral. Cooling tubes 14 have a cross-sectional dimension which corresponds to the thickness of the planar body forming the subcompartment 12, and, therefore, have substantially the same width or depth as that of the channel 16. The cooling tubes 14 may be affixed to the side walls of the channel 16 by gluing, welding, or other suitable method of affixation as may be known in the art, the cooling tubes may be molded directly into the material forming the planar body of the subcompartment 12, or the cooling tubes 14 may be extruded or Otherwise formed as an integral part of the planar body of the subcompartment 12.

Sufficient cooling of the sample volume in the cavity is achieved only when the entire volume of the sample fluid is in close proximity to the surface area of the heat exchange means 14. It has been found preferable to have the sample fluid within a range of about 0.05 cm to about 0.15 cm away from any heat exchange means 14 surface to provide effective cooling of the sample fluid. Thus, the desirable width of channel 16, as measured by the lateral distance between the two parallel cooling tubes 14 is from about 0.1 cm to about 0.3 cm.

Providing internal cooling adjacent to the separation chamber permits use of a higher applied potential for the separation process which increases both the resolution and the speed of the separation. An advantage of the apparatus according to the present invention over designs of the prior art is the configuration of a long narrow separation chamber having internal cooling. As long as the ratio of cooling surface area to process volume remains constant or is increased, the device can be scaled to any sample cavity volume desired, simply by increasing the length and the number of subcompartments 12, without loss of resolution.

An alternative system design for the IEF mode, which increases sample volume processing, features the alignment of two or more subcompartments 12 in series. Instead of constructing an electrophoretic cell having longer subcompartments 12 and, therefore longer channels 16, two or more subcompartments 12 may be employed in series. In this manner, an awkwardly elongated cell design is avoided. A serial arrangement of subcompartments 12 permits application of a higher voltage to the downstream array. As the sample solution is pumped through the separation chamber channel 16 while exposed to a voltage gradient perpendicular to the sample flow and membranes 17, there is a decrease of conductivity in the direction of the sample flow due to the formation of the pH gradient where buffer components become less changed. The loss in conductivity permits application of greater voltages across the cell. In standard electrophoretic cell designs, it is impossible to provide a compensating increased voltage for only that part of the separation chamber which experiences the loss of conductivity of the fluid sample. However, by providing two or more subcompartments 12, in series, according to the present invention, a different voltage may be applied to each serial subcompartment 12 array. Therefore, the effect of conductivity loss because of the ongoing separation, i.e., depletion of charged particles, permits higher voltages, resulting in better and faster separation results.

According to the preferred embodiment of the invention, and the best mode contemplated for the invention, for zone electrophoresis, counter-flow gradient focusing or isoelectric focusing, it is desirable to employ from ten to twelve subcompartments 12 in the array. Fewer than 10 subcompartments compromises separation, while more than 20 subcompartments complicates construction of the apparatus without further improving the separation to a significant extent. For electrodialysis, a single subcompartment may be used in conjunction with an anode and cathode, wherein an appropriate anion and cation exchange membrane, is interdisposed between the anode and cathode, respectively, and the subcompartment.

The above described electrical separator is a versatile instrument for the separation of proteins, cells and salts. It may operate according to various electrophoretic separation principles, for which different operational modes are required. The electrical separator of the present invention is easily adapted to various modes simply by altering the number of subcompartments, the selection and arrangement of membranes, buffers and anion or cation exchange resins. The present invention is, therefore, a unique versatile apparatus.

When the apparatus of the present invention is used for IEF, a pH gradient is created in the array. The pH gradient and, therefore, the resolution, may be easily adjusted by manipulating the buffers inherently required for the isoelectric focusing process. Such adjustment may occur by, for example, judiciously tailoring the gradient either with isoelectric focusing buffers having appropriate pH ranges selected from commercial sources, by prefractionation of commercial pH gradient mixtures in order to produce a more narrow pH gradient than commercially available, or by using mixtures of simple buffers. Most conveniently applicable are ampholyte buffers which are commercially available in the pH range of 3.0 to 10.0 in intervals of 0.01 pH units. By using these buffers a virtually continuous pH gradient may be created in the direction of the electric field in the separation cell.

The method is applied such that unprocessed fluid containing a desalted sample is mixed with the appropriate carrier ampholyte buffer and then pumped directly into each subcompartment of the separation cell. The sample and buffer mixture is continuously pumped into the cell using a multichannel pump 60. While it moves through the cell, it is continuously processed. The processed fluid is then pumped from each of the focusing subcompartments 12 into individual collection vessels 40 by the same pump 60. Thus, an apparatus with 12 subcompartments will require a 24 channel pump.

Using the multichannel pump, the apparatus is first primed with the unprocessed sample fluid, whereby the exit ports lead back to the unprocessed fluid container. Next, the coolant is circulated through the cooling tubes allowing sufficient time for the temperature equilibration. When the temperature equilibrium is achieved in the apparatus, the electrical power is applied. The fluid collected at the exit ports is recycled into the unprocessed sample fluid reservoir until an element of sample has had sufficient time to traverse the length of the cell while exposed to the electric field. The fluid flowing from the exit ports is not recycled and is then continuously collected.

As an example, which is not intended to limit the scope of the invention, a ten subcompartment array 10 is provided, with each separation chamber channel 16 having a volume of 3 ml, providing a total sample cavity volume of 30 ml is provided. The multi-channel pump 60 is set to introduce and withdraw at the rate of 0.5 ml/min per channel. It, therefore, will require 6 min for the sample to complete one pass through the separation chamber channel 16 in each subcompartment 12. Thus, 6 min from the initial application of the power the sample withdrawn from the collection port 13 may be fed directly into the appropriate collection vessels 40.

Complete separation time depends upon a large number of variables such as the steepness of the pH gradient, the concentration of the sample constituents, the amount of power applied, and the magnitude of the protein mobility.

In all IEF devices, the criterion for the resolution of sample components is whether two proteins having closely spaced isoelectric points may be resolved, or, at which minimum isoelectric point difference, between the two sample components, may they still be resolved.

As the resolution increases with the applied voltage gradient, maximizing the voltage is essential for a fast and clean separation. However, the voltage maximum in IEF is limited by the efficiency of heat removal from the sample solution. The more efficient cooling provided by the present invention permits application of higher applied voltages to the apparatus of the invention compared with the IEF apparatus of the prior art. For example, a comparison of the apparatus of the present invention with the ROTOFOR system of the prior art (Table 1) shows that the apparatus of the present invention is superior in its heat removal properties while permitting use of greater maximum applied voltages. The maximum applied power of the present invention is compared with the ROTOFOR having a ceramic cooling tube, 8.6 cm long and 1 cm in diameter, which effectively removes 15 watts. Maximum heat removal is calculated by multiplying the total cooling tube surface area of the apparatus of the present invention by the ratio 15/ROTOFOR cooling tube area.

TABLE 1

| | ROTOFOR | Present Invention (10 subcompartments) |
| --- | --- | --- |
| Fluid Volume (ml) | 45 | 30 |
| Applied Voltage (V) | 1000 | 500 |
| Focus. Distance (cm) | 15 | 3 |
| Potential Gradient (V/cm) | 70 | 170 |
| Cell Length (cm) | 15 | 50 |
| Cooling Surface Area (cm$^2$) | 50 | 470 |
| Max. Current (mA) | 25 | 500 |
| Applied Power (W) | 15 | 200 |
| Cooling Surface/Heat | 3.3 | 4.7 |

Thus, the apparatus of the present invention permits a higher applied field strength with a concomitant greater heat removal capacity than ROTOFOR device. Both effects result in a greater resolution and throughput.

Another advantage of the apparatus of the present invention is that material separated in the flow-through mode may be collected in as little time as is required for the sample to traverse one length of the cell. Where, for example a flow rate of 1 ml/min is employed, the focused material may be collected after only three minutes from the onset of the applied potential. This facilitates rapid analysis of the eluate during the run, which permits adjustments of the operating parameters, if needed, during the run.

Figure 5:
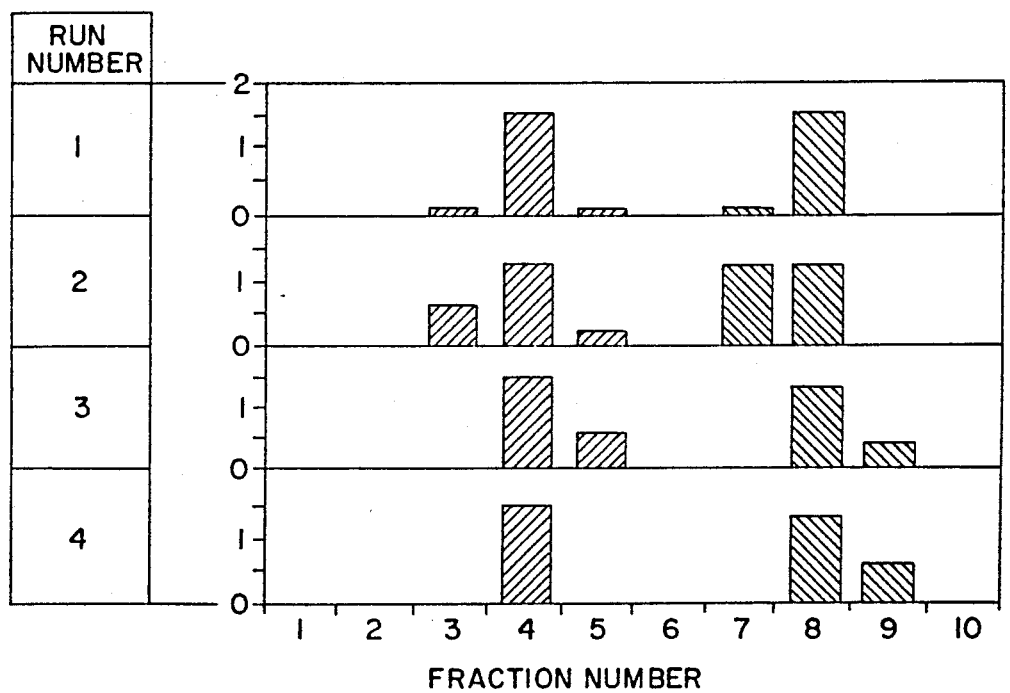
FIG. 5 diagrammatically illustrates fractionation of human serum albumin and human hemoglobin by IEF using the separation apparatus of the present invention.

FIG. 5 presents the results of a separation of a two component mixture of human hemoglobin and human serum albumin by IEF using the electrical separator 10 of the present invention. The process was carried out in an IEF solution containing 1.0 ml of human hemoglobin (80 mg/ml) and 0.5 ml of blue stained human serum albumin (250 mg/ml) diluted to 500 ml with 1% (w/v) pentaethylenehexamine carrier ampholyte. Ion exchange membranes were configured in IEF orientation. Absorbance of the human serum albumin was measured at 602 nm and absorbance of human hemoglobin was measured at 540 nm. The experimental conditions are summarized in Table 2.

TABLE 2

| Run | Applied Potential (V) | Maximum Current (mAmp) | Applied Power (W) | Flow Rate (ml/min) |
| --- | --- | --- | --- | --- |
| 1 | 900 | 200 | 180 | 2.0 |
| 2 | 920 | 210 | 200 | 1.0 |
| 3 | 500 | 85 | 43 | 2.0 |
| 4 | 937 | 266 | 250 | 3.8 |

The data illustrates that a complete separation of the components was accomplished utilizing the apparatus 10 of the present invention in the continuous IEF mode under various conditions which influence the resolution and focusing of the separation.

For a batch operation, the entire sample solution containing the appropriate buffer system is introduced through the inlet ports 11 into the subcompartments 12 of the apparatus 10, and are contained within the separation chamber 16. The pump is turned off to induce the separation process on a non-flowing sample. When the separation is complete, the fractions are collected at the respective outlet ports of the subcompartments by pumping them into the individual collection vessels.

Another separation mode in which the apparatus 10 of the present invention operates has been termed by the inventors counter-flow gradient focusing mode. Counter-flow gradient focusing fundamentally operates on the principle of zone electrophoresis whereby components separate due to their electrophoretic mobility through a medium. In a fixed amount of time, species of a high electrophoretic mobility move further in an electrophoretic field than species of a low electrophoretic mobility.

Conventional zone electrophoresis processing is performed when the direction of the flow increases the speed in the direction of the electrophoretic migration. The counter flow process described in O'Farrell, U.S. Pat. No. 4,323,439 contemplates introduction of the carrier fluid flow in a direction opposite to the direction of the electrophoretic migration of the ions to be separated, thereby slowing the ion migration down at a constant rate of change along the longitudinal separation axis of the separation cell.

According to the present invention, however, there is provided a superimposed counter-flow gradient which counteracts the electrophoretic migration along the focusing axis of the separation cell. The counter-flow gradient, as distinguished from the uniform counterflow employed by O'Farrell, evenly slows migration to create a second separation factor, which, in conjunction with the electrophoretic mobility of the particles, results in focusing and better separation. The length of the separation chamber 16 between the input 11 and outlet 13 ports, in the present invention, is much greater than the distance between adjacent chambers 16 or subcompartments 12. This permits ample time for particles reach equilibrium between the counter-flow gradient and their electrophoretic mobility before the particle exit from the outlet port 13.

FIG. 6 is a schematic representation of the counter-flow gradient focusing mode of the present invention. Unlike the IEF mode, where each of the subcompartments of the separation cell is provided with an inlet and an exit port, in the counter-flow gradient mode the sample fluid is introduced only into an end subcompartment 12 on the array. The remaining inlets 11 are plugged or otherwise blocked. A flow of the fluid sample in buffer, having a flow rate $F_i$, is introduced into the end subcompartment 12 and pumped into the apparatus 10 on a continuous mode. All collection ports 13 are open. The pump 60 withdraws an even fractional portion of the flow pumped out of the collection port 13. Withdrawal of the separated fluid from each subcompartment 12 occurs at a withdrawal flow rate of $F_w$ in which $F_w = F_i/\#$ of subcompartments in the array. In this manner, each adjacent membrane 17 has a decreasing counterflow across it. Thus, for example, if a introductory counter flow consists of 10 units of flow, a ten subcompartment array, one unit of flow is withdrawn from collection port 13 of subcompartment A, and nine units of flow must cross the membrane to the adjacent subcompartment B. In the adjacent subcompartment B, one additional unit of flow will be withdrawn from its collection port 13, and eight units of flow will cross the boundary to the next subcompartment C. The counterflow opposing the direction of electrophoretic velocity, from subcompartment to subcompartment, is thereby reduced by one unit each time and a linear counterflow step gradient is created. For ions electromigrating opposite the fluid flow, the counterflow is accordingly strongest at the final destination of the migrating particles an increases in the direction of migration of the particles.

The resolution of the counter-flow gradient focusing separation has also been increased by imposing an additional counterflow on top of the counter-flow gradient. An illustration of this is a case where a population consisting of two different particles with similar electrophoretic mobilities focus together in a subcompartment bracketed by counterflows of $4\times$ in and $3\times$ out with an electric field strength of Z. All particles in this subcompartment have electrophoretic mobilities which give them a velocity in the electric field Z which is greater than $3\times$ but less than $4\times$. If the electric field Z is increased four times to $4z$, the particles focused between counterflows of $4\times$ and $3\times$ now move four times faster and focus between $16\times$ and $12\times$ counterflows. An additional counter flow of $10\times$ is introduced into subcompartment A, and this $10\times$ counterflow is withdrawn from subcompartment J. The counterflows between the 10 subcompartments, which originally ranged form $9\times$ to $1\times$, now range from $19\times$ to $10\times$. The particles which previously focused in a single subcompartment, between counterflows of $4\times$ and $3\times$, now focus in four subcompartments bracketed by counterflows of $16\times$ and $12\times$. Resolution is, therefore, increased four times, which allows separation of the two particle groups originally focused in the same subcompartment.

As the counterflow opposes the electrophoretic migration, it is possible to adjust the counterflow by controlling the pump speed, as well as the electrophoretic movement by changing the applied voltage. The two opposing forces interact such that each of the various species in the mixture will seek the compartment where the two opposing forces, i.e., the electrophoretic mobility of that particular species and the counterflow at that particular point of the gradient, are equivalent and have a net effect of zero velocity for the component species. When the component attains its stationary position it is said to be focused. The components will remain in their respective compartments until collected.

In a further embodiment of the present invention, one or more of the subcompartments may have inlet ports for the introduction of the sample solution. The sample solution may be introduced into any one of the inlet ports of the sample subcompartments with one unit of inlet flow. When this configuration is employed, an additional unit of flow must be withdrawn from this subcompartment in order to compensate for the additional unit of flow.

In order to start the separation process, the separation cell is first primed with the buffer fluid as to expel all air, whereby the inlet tubes 11 (one for each sample subcompartment) can be joined together to fill the separation cell with the buffer solution by using a pump. After filling the cell, the sample to be separated may then either be introduced into the buffer reservoir or pumped directly into the subcompartment 12 of choice.

In order to begin separation, the cooling system must be switched on and, after a temperature equilibrium is reached between the coolant and the buffer fluid, the power supply is turned on. Depending on the power supply means, the limits of the applied power, the applied voltage and the applied current must be previously determined. Typical limits may be 100–200 V, 100–200 W, and 100–200 mA. These limits depend on many factors, including the buffer conductivity, the magnitude of the counterflow gradient and the cooling rate.

Each of the exit tubes is connected to its respective collection vessel. The sample collection may thus be performed in a continuous and automatic manner.

Table 3 presents the results of a separation of two colored proteins, human hemoglobin (Hb) human serum albumin (A), introduced in three runs at different subcompartment input positions. In the first run, the protein solution was introduced at subcompartment B, in the second run the sample mixture was pumped into the subcompartment E and in the third run the sample mixture was input into subcompartment G. A counterflow of $10\times$ was introduced into subcompartment A adjacent to the anode. The results clearly show that successful separation for all three experiments was achieved. The two proteins were collected in separate fractions from different subcompartments without any overlap.

TABLE 3

| input position Subcompartment | fraction number | | | | | | | | | |
|---|---|---|---|---|---|---|---|---|---|---|
| | A | B | C | D | E | F | G | H | I | J |
| B | — | — | A | A | — | Hb | Hb | — | — | — |
| E | — | — | A | A | — | Hb | Hb | — | — | — |

TABLE 3-continued

| input position Subcompartment | fraction number | | | | | | | | | |
|---|---|---|---|---|---|---|---|---|---|---|
| | A | B | C | D | E | F | G | H | I | J |
| G | — | — | A | A | — | Hb | Hb | — | — | — |

All three experiments were run at the same counterflow input and the same voltage. The results clearly indicate that the Albumin exited the separator in subcompartments C and D, while the Hemoglobin exited in subcompartments F and G with a clear subcompartment E therebetween. These results also demonstrated that the position of the introduction of the proteins does not influence focusing position. A protein is focused by attaining its balance between electrophoretic velocity and the counterflow and always migrates into its respective fraction defined by its electrophoretic properties. That the final position of the protein focusing is independent of its input position confirms that the counterflow gradient focusing mode of the present invention is not a zone electrophoresis methodology, since the final position in zone electrophoresis will depend on the input position.

Conventional zone electrophoresis, of course, may be performed in the apparatus of the present invention as well by simply omitting the counter flow gradient principle.

FIG. 7 is a schematic representation of yet another embodiment of the present invention relating to the application of the apparatus of the present invention for electrodialysis, whereby the principle of electrophoresis and a continuous flow operation are employed.

The configuration of a preferred embodiment comprises one subcompartment 12 with two electrode compartments 30, 32 on either side. The compartments are separated by ion exchange membranes 19. The sample to be treated is introduced through the inlet port 11 of the subcompartment 12 and exits through the collection port 13 at the opposite end of the subcompartment 12.

The electrodialysis device according to this embodiment of the invention is operated such that the sample solution is pumped into the subcompartment 12 in such a manner to first expel all the air in the separation chamber channel 16. When the channel 16 is filled with the sample solution, electrical current is applied at preset voltage, current and power limits. The ionic species, which are continuously pumped into the subcompartment 12, migrate under the electrophoretic force through the ion exchange membranes into the electrode compartments, leaving the depleted or cleaned solution behind, which may be continuously pumped off at the exit ports.

The effectiveness of the electrodialysis method of the present invention was demonstrated by desalting water which contained 0.15M NaCl.

Finally, according to another embodiment of the present invention, the present invention contemplates a water purification process, in which pathogenic organisms, toxins and/or heavy metals may be separated, concentrated and removed from a water sample. Waste water may contain pathogenic organisms, toxins and heavy metals. The water purification process of the present invention is useful in generating potable water from waste streams, gray water, or industrial or agricultural waste streams containing one or more of pathogenic organisms, toxins, toxic metals, and colloidal soil particles. The water purification process is particularly useful in bioregenerative closed systems required in confined environments such as in spacecraft or submarines where recycling of water is a necessity.

According to the present invention, there is provided a method of water purification which employs the counterflow gradient focusing methodology and continuous flow electrodialysis previously disclosed. Standard buffer systems may be employed as a counterflow buffer solution. Alternatively, an acid and a base pair may be introduced into the anode and cathode electrodes, respectively, whereby no flow of the respective ions across the separation cell occurs since the respective ions are already at their destination. If, for example, NaOH is introduced into the cathode compartment and $H_2SO_4$ is introduced at the anode, the $Na^+$ ion remains at the cathode and the $Cl^-$ ion stays at the anode; no electrolyte transport is observed. Alternatively, standard buffers such as tris acetate, pH 7.2. can be used as electrolytes to furnish the buffering ions to the separation chamber to facilitate the removal of pathogens and toxins containing ionizable functional groups. The buffers used in this process are subsequently removed in tandem by continuous flow electrodialysis in the present invention from the water in those subcompartments that do not contain pathogenic organisms or pathogens.

Water samples containing heavy metal ions and pathogens have been purified successfully with the above described counterflow gradient focusing method. As an example, which is not intended to be limiting of the scope of the invention, lead has been separated from a waste stream containing *E. Coli* and *Rhizobia* using the counterflow focusing methodology. A twelve subcompartment array was employed as previously discussed. As summarized in Table 4, there was a sharp focusing of lead ions, with minimal or no presence of lead ions noted in other subcompartments of the apparatus.

TABLE 4

| Run | % Pb/Subcompartment | | | | | | | | | | | |
|---|---|---|---|---|---|---|---|---|---|---|---|---|
| | 1 | 2 | 3 | 4 | 5 | 6 | 7 | 8 | 9 | 10 | 11 | 21 |
| 1 | 3 | <0.5 | 0 | 0 | 0 | 0 | 0 | <0.5 | 94 | 1 | 1 | 1 |
| 2 | 0 | 0 | 0 | 0 | 0 | 4 | 6 | 12 | 10 | 68 | 0 | 0 |

The sharp focusing which can be achieved with the counter flow gradient leads to the concentration of undesired materials into very small volumes in certain subcompartments, while maximizing the volume of purified water in other subcompartments. The contaminants may thus be removed from those specific subcompartments, while purified water may be pumped off others in a continuous mode.

The effectiveness of the separation process for biological materials may be monitored visually, using bioluminescent assay and/or the polymerase chain reaction employing specific gene probes.

The present invention is, of course, in no way restricted to the specific disclosure of the specification, examples and drawings, but also encompasses any modifications within the scope of the appended claims.

What is claimed is:

1. An apparatus for multi-modality electrophoretic separations of component charges species from a solution, comprising:
   a plurality of planar spacers, each spacer having a generally elongate planar shape defined by front and back planar surfaces thereof, top and bottom edges thereof and lateral edges thereof and a longitudinal opening defining a narrow longitudinal separation chamber in each of said plurality of planar spacers, said longitudinal separation chamber being open to the front and back surfaces of the planar spacer and having top, bottom and opposing lateral edges defined by the planar spacer;

at least one solution inlet port and at least one opposing solution outlet port passing through said top and bottom edges of each of said plurality of planar spacers and in fluid flow communication with said separation chamber;

a plurality of elongate tubular cooling members associated with said opposing lateral edges of said longitudinal separation chamber, said cooling members having high thermal conductance properties and a surface area which contacts the solution in said separation chamber;

a plurality of ion non-selective permeable membranes, at least one of said plurality of ion non-selective permeable membranes being interdisposed between a front surface and a back surface of a pair of adjacent planar spacers thereby defining a boundary between the respective separation chambers of the adjacent pair of adjacent planar spacers and oriented generally parallel to the direction of flow of the sample solution within said separation chamber;

at least one cooling member inlet port and at least one cooling member outlet port, each in fluid flow communication with said plurality of cooling members, wherein said at least one cooling member inlet port conducts a cooling medium from an external source into said plurality of cooling members and said at least one cooling member outlet port conducts the cooling medium from said separation chamber;

means for applying an electrical potential to the sample solution within said separation chamber; and a multi-channel pump for pumping the solution into said solution inlet port of said planar spacer and withdrawing solution from said solution outlet port.

2. The apparatus according to claim 1, wherein each of said plurality of planar spacers further comprises a thin generally rectilinear resilient member having a longitudinal aspect greater that a lateral aspect.

3. The apparatus according to claim 2, Wherein said separation chamber is centrally oriented along the longitudinal aspect of said rectilinear resilient member and passes through a lateral axis of said rectilinear member.

4. The apparatus according to claim 3, wherein each of said plurality of planar spacers further comprises a dielectric material.

5. The apparatus according to claim 4, wherein said dielectric material is silicone rubber.

6. The apparatus according to claim 1, wherein said cooling members further comprise tubular members have a quadrilateral cross-section.

7. The apparatus according to claim 4, wherein said cooling members further comprise tubular members have a circular cross-section.

8. The apparatus according to claim 4, Wherein said tubular members further comprise a plastic material.

9. The apparatus according to claim 8, wherein said plastic material is selected from the group consisting of tetrafluoroethylene, fluorinated ethylpropylene resins, polypropylene co-polymers, polyethylene and silicone.

10. The apparatus according to claim 1, wherein each of said plurality of ion non-selective permeable membrane further comprises a woven monofilament screen.

11. The apparatus according to claim 1, wherein said plurality of planar spacers are co-joined to form a parallel array of said planar spacers, and said cooling fluid inlet ports, in each of said plurality of planar spacers, are co-axially aligned, thereby forming a cooling fluid inlet channel passing through said parallel planar spacer array and said cooling fluid outlet ports, in each of said plurality of planar spacers, are co-axially aligned, thereby forming a cooling fluid outlet channel passing through said parallel planar spacer array.

12. The apparatus according to claim 1, wherein said means for applying an electrical potential further comprises a direct current power source coupled to at least one anode and at least one cathode.

13. The apparatus according to claim 12, wherein said at least one anode and said at least one cathode each further comprise an end plate compartment adapted to receive said anode or said cathode, and contain a respective anolyte or catholyte therein.

14. The apparatus according to claim 12, wherein said at least one anode further comprises at least one anion exchange membrane operably associated therewith and said at least one cathode further comprises at least one cation exchange membrane operably associated therewith.

15. The apparatus according to claim 12, wherein said apparatus further comprises recirculating means for recirculating each of said anolyte and said catholyte.

16. A method for separating charged components in a fluid mixture, comprising the steps of:

providing a separation apparatus comprising a plurality of adjacent parallel longitudinal separation chambers having ion non-selective permeable membranes interdisposed therebetween, thereby defining a longitudinal fluid flow path within each of said plurality of adjacent parallel longitudinal separation chambers and a component mobility path between said adjacent separation chambers, each of said plurality of longitudinal separation chambers further having tubular cooling members disposed in and forming lateral edges of each of said separation chambers for locally cooling the fluid mixture only within the respective separation chamber with which said cooling members are associated;

recirculating a cooling medium through said cooling members and establishing a thermal equilibrium within each of said separation chambers and across adjacent parallel longitudinal separation chambers;

introducing the fluid mixture into at least one longitudinal separation chamber;

applying an electrical potential across said plurality of the separation chambers to impart electrophoretic velocity to the components in the fluid mixture; and continuously recirculating said cooling medium through said cooling means to dissipate Joule heat from the fluid mixture during application of said electrical potential.

17. The method according to claim 16, further comprising the steps of establishing a pH gradient across said plurality of adjacent longitudinal separation chambers and separating constituents of a mixture of two or more components by the principals of isoelectric focusing whereby each component migrates under the influence of the electric field to its pH corresponding to its isoelectric point.

18. The method according to claim 16, wherein said step of applying an electrical potential further comprises establishing a stable voltage gradient along the longitudinal axis of each of said plurality of separation chambers.

19. The method according to claim 16, wherein said step of introducing the component mixture further comprises continuously flowing the component mixture into said at least one longitudinal chamber.

20. The method according to claim 19, further comprising the steps of continuously withdrawing separated fluid from said at least one longitudinal chamber to establish a continuous flow therein.

21. The method according to claim 17, wherein said at least one component is a protein.

22. The method according to claim 17, wherein said at least one component is selected from the group consisting of organic and inorganic compounds.

23. The method according to claim 17, wherein said at least one component is a heavy metal.

24. The method according to claim 17, wherein said at least one component is a pathogen.

25. The method according to claim 17, wherein said at least one component is a colloidal soil particle.

* * * * *